US011273437B2

(12) United States Patent
Koike et al.

(10) Patent No.: US 11,273,437 B2
(45) Date of Patent: Mar. 15, 2022

(54) CELL TREATMENT APPARATUS

(71) Applicant: Rohto Pharmaceutical Co., Ltd., Osaka (JP)

(72) Inventors: Tetsuo Koike, Osaka (JP); Masahiro Takimoto, Osaka (JP); Yoshiki Yagi, Osaka (JP)

(73) Assignee: Rohto Pharmaceutical Co., Ltd., Osaka (JP)

( * ) Notice: Subject to any disclaimer, the term of this patent is extended or adjusted under 35 U.S.C. 154(b) by 507 days.

(21) Appl. No.: 15/764,731

(22) PCT Filed: Oct. 19, 2016

(86) PCT No.: PCT/JP2016/080944
§ 371 (c)(1),
(2) Date: Mar. 29, 2018

(87) PCT Pub. No.: WO2017/069149
PCT Pub. Date: Apr. 27, 2017

(65) Prior Publication Data
US 2018/0290136 A1 Oct. 11, 2018

(30) Foreign Application Priority Data
Oct. 20, 2015 (JP) .............................. JP2015-206194

(51) Int. Cl.
*B01L 1/02* (2006.01)
*B25J 21/02* (2006.01)
(Continued)

(52) U.S. Cl.
CPC ............. *B01L 1/025* (2013.01); *B25J 21/005* (2013.01); *B25J 21/02* (2013.01); *C12M 1/00* (2013.01);
(Continued)

(58) Field of Classification Search
CPC ........ C12M 23/44; C12M 41/14; C12M 1/00; C12M 37/00; B25J 21/005; B25J 21/02; B01L 1/025; B01L 2200/16
See application file for complete search history.

(56) References Cited

U.S. PATENT DOCUMENTS

2004/0215362 A1 10/2004 Kokubo et al.
2005/0260742 A1 11/2005 Watanabe

FOREIGN PATENT DOCUMENTS

EP 1571201 A2 9/2005
JP 2002-310474 A 10/2002
(Continued)

OTHER PUBLICATIONS

European Search Report dated June 6, 2 019 in connection with European Patent Appl. No. 16857462.2.
(Continued)

*Primary Examiner* — Gautam Prakash
(74) *Attorney, Agent, or Firm* — Brooks Kushman P.C.

(57) ABSTRACT

Provided is a cell treatment apparatus that includes: an isolator; a disposal box that includes a storage part; and a decontamination unit, wherein the disposal box includes: a first opening and closing device that is configured to allow the isolator and the storage part to be communicated with each other at the time of disposal of the waste product and allow them to be shut off from each other after the putting-in of the waste product and before the disposal of the same; and a second opening and closing device that is configured to allow the storage part and the outside to be communicated with each other at the time of disposal of the waste product, which has been put into the storage part, and allow them to be shut off from each other after the disposal of the waste product.

6 Claims, 10 Drawing Sheets

(51) Int. Cl.
  *C12M 3/00* (2006.01)
  *B25J 21/00* (2006.01)
  *C12M 1/00* (2006.01)
  *C12M 1/12* (2006.01)

(52) U.S. Cl.
  CPC ............ *C12M 23/44* (2013.01); *C12M 37/00* (2013.01); *C12M 41/14* (2013.01); *B01L 2200/16* (2013.01)

(56) References Cited

FOREIGN PATENT DOCUMENTS

| | | |
|---|---|---|
| JP | 2004-229619 A | 8/2004 |
| JP | 2005-204547 A | 8/2005 |
| JP | 2005-235882 A | 9/2005 |
| JP | 2007-037422 A | 2/2007 |
| JP | 2009-291104 A | 12/2009 |
| JP | 2010-161931 A | 7/2010 |

OTHER PUBLICATIONS

Katsumi Nakashima et al., "Kansaibo no Jido Baiyo System", 2014, Biotechnology, vol. 92, No. 9, pp. 473 to 478 (See attached English translation of the International Preliminary report).
IPR issued May 3, 2018 in connection with PCT/3P2016/080944.

CELL TREATMENT APPARATUS

CROSS-REFERENCE TO RELATED APPLICATION

This application claims priority to Japanese Patent Application No. 2015-206194, the disclosure of which is incorporated herein by reference in its entirety.

FIELD

The present invention relates to a cell treatment apparatus that includes an isolator for cell treatment.

BACKGROUND

In recent years, cell culture is performed using tissues and cells of various sites of human body, fertilized eggs, or the like, and the cultured cells have been put to practical use for regenerative medicine. In the cell culture, it is important to prevent contamination of cells by bacteria or the like during the culture. Therefore, an automatic culturing apparatus as an example of a cell treatment apparatus that enables the culture of cells in a housing that can maintain thereinside in aseptic conditions has been already proposed.

The aforementioned automatic culture apparatus is constituted by arranging a culture treatment apparatus thereinside, which includes, in a housing, a culturing chamber for storing culturing vessels for culturing cells, a conveyance robot for taking out the culturing vessels from the culturing chamber, and a plurality of robots for transferring therebetween the culturing vessels taking out using the conveyance robot and allowing them to be subjected to various treatments such as exchanging culturing media of the culturing vessels and supplying medicines. The culture treatment apparatus has an inner space and includes a first partition wall that is configured to partition the inner space into an upper space and a lower space, and has a waste port for disposal of used tips, and a duct that has an upper end opening connected to the waste port to be in communication with each other, a lower end opening of the duct being connected to a waste container to be in communication with each other. The culture treatment apparatus further includes thereinside a plurality of storage tanks for storing waste liquid to be disposed of as a result of the exchanging of culturing media (for example, Patent Literature 1)

CITATION LIST

Patent Literature

Patent Literature 1: JP 2005-204547 A

SUMMARY

Technical Problem

According to the configuration of Patent literature 1 mentioned above, while including the waste container for the disposal of the used tips and the storage tank for the storage of the waste liquid, it does not include a waste part for disposal of plural kinds of containers, such as culturing vessels with liquid inside disposed of, as a result of which they are no longer needed, and empty containers with no contents inside as a result of using medicines. These no longer usable containers have a relatively larger size compared with the tips and thus pose a problem mentioned below. Specifically, there is a case where the inside of the culture treatment apparatus is filled with culturing vessels or empty containers which have become no longer needed, during the treatment within the culture treatment apparatus, which causes the necessity to once carry out these containers to the outside of the culture treatment apparatus in order to enable the robots to perform treatments. In such a case, it is necessary to return the culturing vessels, which are being treated, into the culturing chamber so that these containers are carried out to the outside of the culture treatment apparatus. Accordingly, there is need for much time, which includes not only the time for returning the culturing vessels into the culturing chamber, but also the time for bringing again the inside of the culture treatment apparatus into aseptic conditions after the carrying-out of the culturing vessels. As a result, there is need for much time for interrupting the treatments, which makes it difficult to achieve efficient mass production and hence poses a problem of causing hindrance in implementing progress of advance of regenerative medicine. This is applicable not only to the automatic culturing apparatus for cell culturing, but also to the cell treatment apparatus in general, which is configured to subdivide the cultured cells and fill them into containers to manufacture products.

The present invention has been conceived in view of the above circumstances. It is an object of the present invention to provide a cell treatment apparatus that enables unnecessary containers, which are generated during treatment, to be disposed of outside the apparatus, while having the inside of the apparatus maintained in aseptic conditions, thereby enabling efficient treatment of cells without interrupting the treatment.

Solution to Problem

A cell treatment apparatus according to the present invention includes: an isolator that has an inner space maintained in aseptic conditions and is configured to treat cells in the inner space; a disposal box that includes a storage part that can be sealed and is configured to allow a container, which contained a reagent for use in treatment of cells in the inner space of the isolator and has become no longer needed as a result of use of the reagent, to be once put thereinto as a waste product and then be disposed of outside the isolator; and a decontamination unit for decontaminating the storage part, wherein the disposal box includes: a first opening and closing device that is openable and closable, and is configured to allow the isolator and the storage part to be communicated with each other at the time of disposal of the waste product and allow them to be shut off from each other after the putting-in of the waste product and before the disposal of the same; and a second opening and closing device that is openable and closable, and is configured to allow the storage part and the outside to be communicated with each other at the time of disposal of the waste product, which has been put into the storage part, and allow them to be shut off from each other after the disposal of the waste product.

The cell treatment apparatus according to the present invention may further comprises an air supply unit for storage part that supplies air into the storage part when the second opening and closing device is opened and the waste product is disposed of.

The cell treatment apparatus according to the present invention may be configured so that the second opening and closing device is formed by a plate-shaped lid that can open and close an opening formed at a lower end of the storage part, and the apparatus further comprises an air supply unit for lid supplies air onto a surface which is located on the storage part side of the lid when the lid is opened and the waste product is disposed of.

The cell treatment apparatus according to the present invention may be configured so that the waste product comprises a container body, and a cap for closing an opening of the container body and thereby sealing the inside thereof, and the waste product is disposed of with the inside of the container body being sealed by the cap.

The cell treatment apparatus according to the present invention may be configured so that the decontamination unit is connected to the storage part.

The cell treatment apparatus according to the present invention may be configured so that the decontamination unit is arranged in or connected to the isolator so that part of a decontamination fluid supplied from the decontamination unit to the isolator is supplied into the storage part.

It is preferable that the cell treatment apparatus according to the present invention includes a pass box for carrying the container into the isolator, and the container, which has been carried into the pass box and used, is put into the disposal box.

DESCRIPTION OF EMBODIMENTS

Hereinafter, an apparatus to produce cultured cell products (hereinafter, referred to as production apparatus) that is an example of a cell treatment apparatus of the present invention will be described. In the following description on the front, rear, left, and right directions, the left and right directions correspond to the state shown in FIG. 1 and FIG. 2, and the front and rear directions correspond to the state of FIG. 2 where the lower side corresponds to the "front" and the upper side corresponds to the "rear" (the directions are shown also in FIG. 2).

Figure 1:
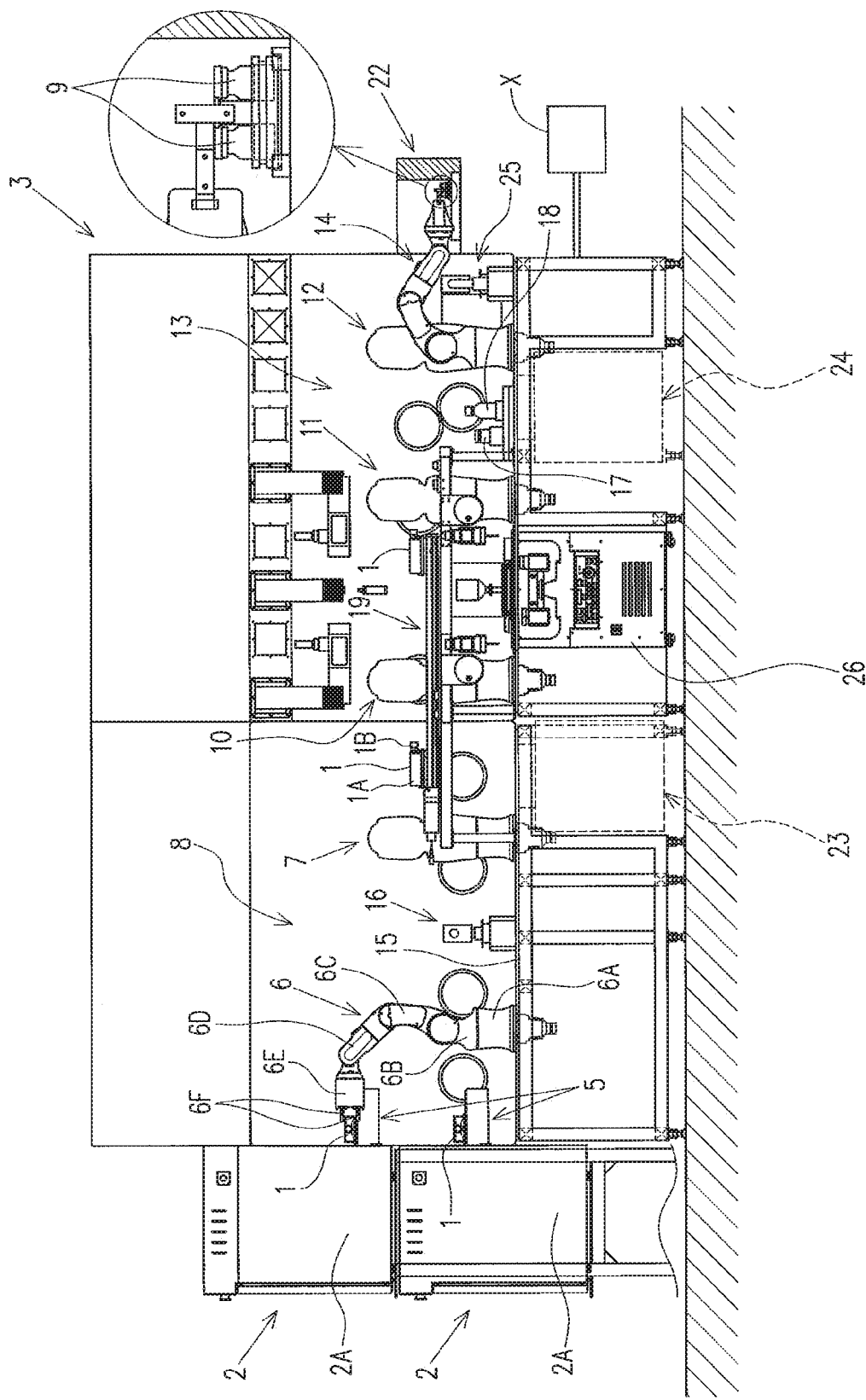
FIG. 1 is a front view of an apparatus to produce cultured cell products of the present invention.
Figure 2:
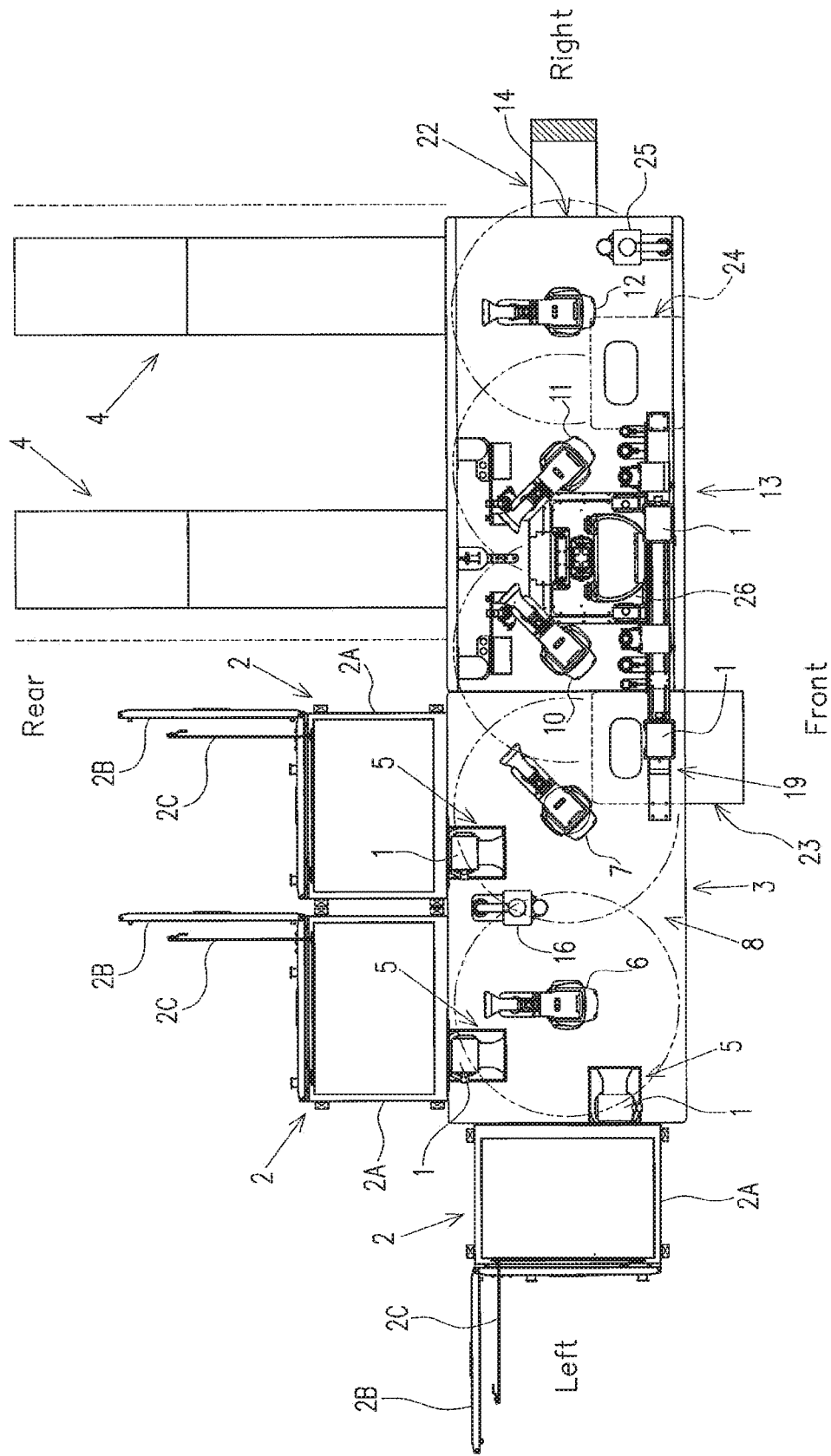
FIG. 2 is a plan view of the aforementioned production apparatus.
Figure 3:
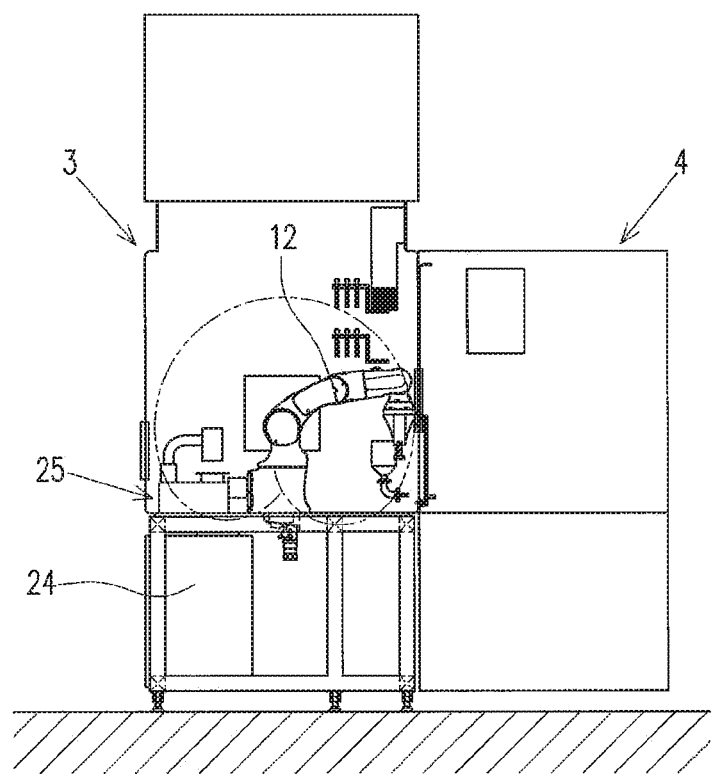
FIG. 3 is a view of the aforementioned production apparatus as seen from the outlet side.

FIG. 1 to FIG. 3 show the production apparatus of this embodiment. The production apparatus includes a plurality of incubators 2 that house cell culture vessels (herein referred to as culture vessels) 1, a horizontally elongated isolator (treatment apparatus) 3 that has an inner space maintained in aseptic conditions and is configured to treat, in the inner space, cells contained in the culture vessels 1 which are conveyed from the incubators 2, and a plurality (two in FIG. 2) of pass boxes 4 that are configured to be capable of carrying articles (including containers containing reagents), the articles being necessary for subdividing and putting-in of cells cultured in the culture vessel 1. As the culture vessel 1, a HYPERFlask (manufactured by Corning Incorporated) capable of culturing cells in multilayers, for example, can be used. The culture vessel 1 includes a container body 1A, and a cap 1B for closing an upper end opening of the container body 1A and thereby sealing the inside thereof. The inside of the culture vessel 1 is sealed with the cap 1B closed when the culture vessel 1 is disposed of, and therefore it is possible to suppress occurrence of leakage of a liquid remaining within the culture vessel 1 to the outside and hence adhering to the inside of a hereinafter mentioned storage part 27S (see FIG. 7). Each part is controlled by a control device X schematically shown in FIG. 1. The control device X may be provided integrally with the production apparatus or may be a separate body (such as a personal computer) connected to the production apparatus in a wired or wireless manner. Further, it is also possible to provide the control device X integrally with the production apparatus and provide only an operation section of the control device X that is operated by an operator (such as a tablet terminal) as a separate body from the production apparatus.

The incubators 2 are provided while being vertically stacked in two stages as shown in FIG. 1. Six units of the incubators 2 are provided in total, at three points in total including one point at the left end of the isolator 3 and two points in the left end part behind the isolator 3, as shown in FIG. 2. Two incubators 2, 2 in the upper stage and the lower stage have the same configuration. Each of the incubators 2 is provided with racks (not shown) capable of housing a large number of the culture vessels 1 within a casing 2A. The casing 2A has a box shape with one lateral side opening so that the culture vessels 1 can be taken in and out through the lateral side. Two doors 2B and 2C configured to close the opening on the one lateral side of the casing 2A are attached to the casing 2A so as to be freely openable. The inside door 2C is formed with, for example, a transparent material, so that the number of the culture vessels 1 housed therein and the state of the cell culture can be checked only by opening the outside door 2B while the opening is closed by the inside door 2C. Further, carbon dioxide gas for adjusting the culture atmosphere is configured to be supplied into the incubators 2. Further, the culture vessels 1 housed on the racks inside the incubators 2 are configured to be delivered onto a plurality of mounting tables 5 provided in the isolator 3 by a delivery mechanism, which is not shown. Six units of the mounting tables 5, which is the same number as the number of the incubators 2, are arranged corresponding to the incubators 2.

As described above, the isolator 3 is horizontally elongated (in this embodiment, it is rectangular in planer view), where one set (two units on the upper and lower sides) of incubators 2 is located on the short side of the isolator 3 (in this embodiment, the left side), and a plurality of sets (in this embodiment, two sets of incubators 2) are located on the longitudinal side (in this embodiment, the rear side). This configuration can reduce the size of the production apparatus without decreasing the number of cultured cells.

The isolator 3 includes an observation section 8 that includes two first robot arms 6 and 7 configured to move the culture vessels 1 to an observation position so that the degree of growth in the culture vessels 1 taken out of the incubators 2 is checked, a processing section 13 that is provided continuously with the observation section 8 and includes three second robot arms 10, 11, and 12 that are configured to perform various processes for transferring cells in the culture vessels 1 that have a specified number of cells out of the culture vessels 1 observed in the observation section 8 into a large number of product containers 9 (such as vial containers, see the enlarged view of FIG. 1), which have been carried in from the pass boxes 4, and an outlet 14 that is configured to allow the large number of product containers 9, into which the cells have been transferred, to be taken out therethrough. A large number of work gloves (not shown) that allow the operator to perform operations by putting their hands into the isolator 3 are attached onto the front and rear walls of the isolator 3. As shown in FIG. 2, the five robot arms 6, 7, 10, 11, and 12 are aligned in a straight line extending in the left and right directions along the longitudinal direction of the isolator 3.

With reference to the left and right directions, the first robot arm 6 on the left side corresponds to one set of incubators 2 located on the short side of the isolator 3 (in this embodiment, on the left side) and one set of incubators 2 on the left side out of the sets of incubators 2 located on the longitudinal side (in this embodiment, on the rear side). The first robot arm 6 on the left side can handle the culture vessels 1 that are housed in these incubators 2 (the range that can be reached by each robot arm (in planer view) is shown in FIG. 2 with a dashed-double-dotted circle). Further, the first robot arm 7 on the right side corresponds to one set of incubators 2 on the right side out of the sets of incubators 2 located on the longitudinal side of the isolator 3. The first robot arm 7 on the right side can handle the culture vessels 1 housed in the incubators 2.

With reference to the left and right directions, the second robot arm 10 on the left side and the second robot arm 11 in the middle correspond to the pass box 4 on the left side out of the pass boxes 4 located on the longitudinal side of the isolator 3 (in this embodiment, on the rear side). The second robot arm 10 on the left side and the second robot arm 11 in the middle can handle articles and reagents, which are to be housed (or having been housed) in the pass box 4.

The second robot arm 12 on the right side corresponds to the pass box 4 on the right side out of the pass boxes 4 located on the longitudinal side of the isolator 3 (in this embodiment, on the rear side) and a box 22 for carrying out the product containers 9. The second robot arm 12 on the right side can handle containers and reagents, which are to be housed (or having been housed) in the pass box 4, and the product containers 9 to be housed in the box 22.

As seen from the overlapping of the dashed-double-dotted circles shown in FIG. 2, the five robot arms 6, 7, 10, 11, and 12 are arranged in a positional relationship so as to be capable of passing articles to each other.

In this way, the robot arms 6, 7, 10, 11, and 12 are located within the isolator 3, thereby enabling each of the robot arms 6, 7, 10, 11, and 12 to act on the incubators 2, the isolator 3, the pass boxes 4, and the box 22 according to the purpose. Thus, it is possible to improve the working efficiency and contribute to mass production of cultured cell products.

The first robot arms 6 and 7 and the second robot arms 10, 11, and 12 in this embodiment have the same configuration. Therefore, the description will be made only for the first robot arm 7 located at the left end. The first robot arm 6 is constituted by an articulated robot arm. The first robot arm 6 includes a fixed part 6A fixed to a base member 15 of the isolator 3, a base part 6B that is pivotable about the vertical axis at the distal end part of the fixed part 6A, a first arm 6C that is swingable about the horizontal axis at the distal end part of the base part 6B, a second arm 6D that is swingable about the horizontal axis at the distal end part of the first arm 6C, a third arm 6E that is swingable about the horizontal axis at the distal end part of the second arm 6D, and a pair of grips 6F, 6F that are attached to the distal end of the third arm 6E so as to be opposed thereto. The pair of grips 6F 6F are configured to be capable of moving close to and away from each other. As such, the articulated first robot arms 6 and 7 can hold the culture vessels 1 delivered from the incubators 2 using the pair of grips 6F, 6F (see FIG. 1) and move them to a microscope 16 at the observation position. The second robot arms 10, 11, and 12 are configured to hold such as a centrifuge tube 17 and a preparation tank 18 shown in FIG. 1 in addition to the culture vessels 1 so as to be capable of performing various processes.

The microscope 16 located at an observation position is arranged between the two first robot arms 6 and 7. According to such an arrangement of the microscope 16, it is possible to move the culture vessels 1 to the microscope 16 using the first robot arm 6 on the left side so as to observe the cells, and as a result of the observation, it is possible to hold the culture vessels 1 that have been determined to have a specified number of cells so as to rapidly move them to the processing section 13 side, using the first robot arm 7 on the right side. That is, the first robot arm 6 on the left side mainly performs the operation to move the culture vessels 1 to the microscope 16, and the first robot arm 7 on the right side performs the operation to move the culture vessels 1 that have been determined to have a specified number of cells toward the processing section 13 side, so that the operation speed can be accelerated. The determination on whether the culture vessels 1 have a specified number of cells may be made by counting the number of cells by visual inspection of the operator (human) of the production apparatus or may be made automatically by the control device X based on the number of cells calculated by analyzing an image captured by a camera provided in the isolator 3 so as to automatically calculate the number of cells. The culture vessels 1 that are delivered from the incubator 2 located opposed to the first robot arm 7 on the right side are held by the first robot arm 7 on the right side to be moved to the microscope 16. Further, a microscope 25 for observation of cells is provided also in the processing section 13. The object to be placed on an observation stage of the microscope 25, such as a hemocytometer, is held by the second robot arm 12 on the right end to be moved.

The culture vessels 1 after the observation are conveyed not only by being directly passed from the first robot arm 7 on the right side to the second robot arms 10 arranged at the left end of the processing section 13. For example, in the case where the second robot arm 10 is in an operation, the culture vessels 1 are conveyed by a conveying apparatus 19 to a position where the second robot arm 10 at the left end of the processing section 13 or the second robot arm 11 arranged at horizontal center of the processing section 13 can grip them. The conveying apparatus 19 is provided along the front sidewall of the isolator 3 and is set to a length that allows the conveying apparatus 19 to convey them from the right end part of the observation section 8 of the isolator 3 to the horizontal center of the processing section 13. Accordingly, when the first robot arm 7 on the right side passes the culture vessels 1 after the observation to the conveyance starting end part of the conveying apparatus 19, the conveying apparatus 19 conveys the culture vessels 1 to the position where one of the two second robot arms 10 and 11 can grip them.

The conveying apparatus 19 is provided corresponding to at least one robot arm (in this embodiment, the first robot arm 7) located in the observation section 8 and a plurality of robot arms (in this embodiment, the two second robot arms 10 and 11) located in the processing section 13. The first robot arm 7 can directly deliver the articles to the second robot arm 10. The conveying apparatus 19 can deliver the articles to the first robot arm 7 and the third robot arm 11 between which direct delivery of the articles is impossible. Therefore, even in the case where the articles cannot be delivered from the first robot arm 7 to the third robot arm 11 via the second robot arm 10 due to the second robot arm 10 being in operation, the articles can be delivered from the first robot arm 7 to the third robot arm 11 via the conveying apparatus 19. Therefore, the articles can be conveyed in parallel (via a plurality of routes) within the isolator 3. Accordingly, the working efficiency within the isolator 3 can be improved, and thus the productivity can be improved.

Figure 4:
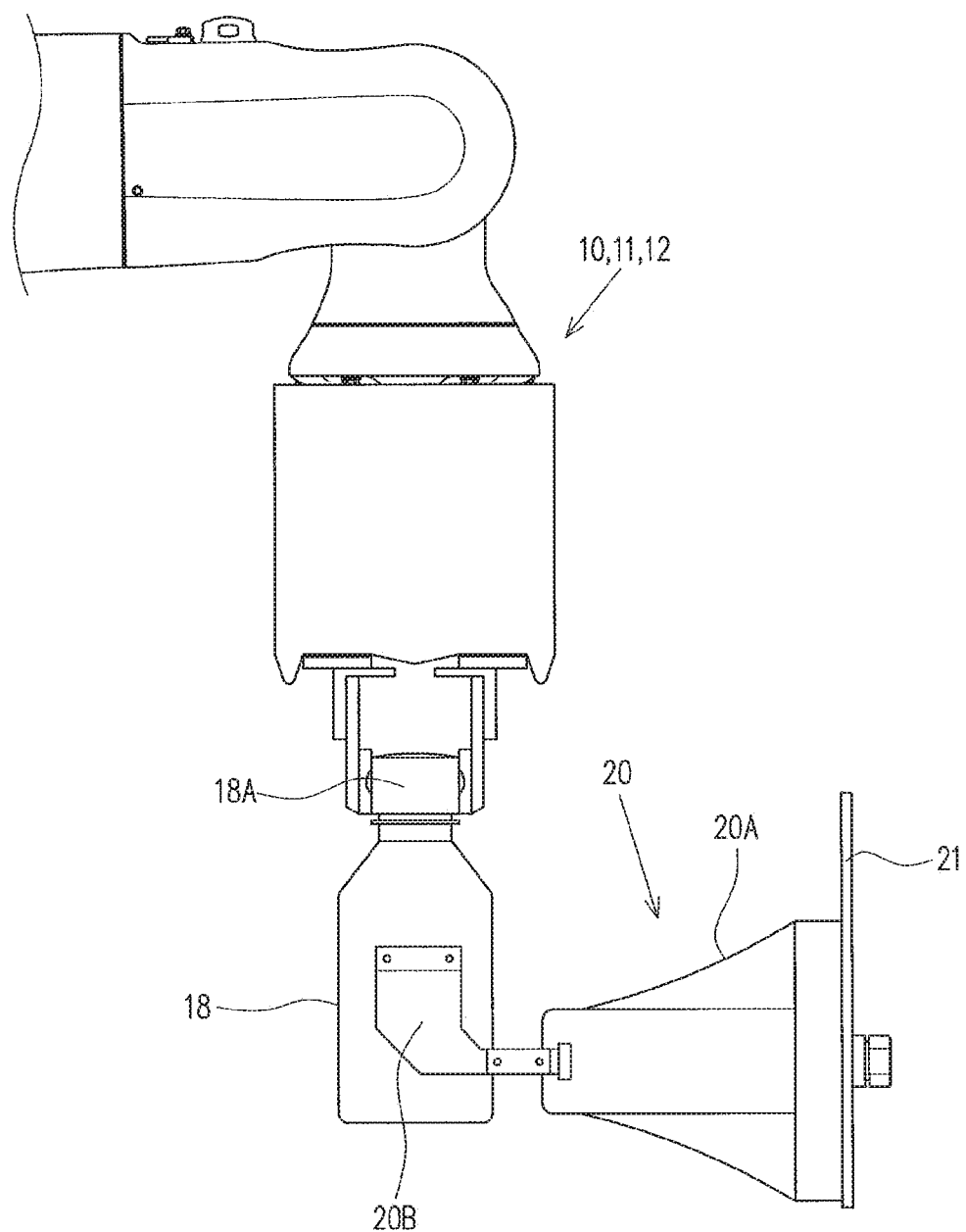
FIG. 4 is an explanatory diagram showing the state immediately before a vessel cap is opened by a robot arm.

In the processing section 13, three units of the second robot arms 10, 11, and 12 are arranged at equal intervals, and the intervals are set to be smaller than the interval between the two first robot arms 6 and 7, so that the speed of various processes performed between the second robot arms 10 and 11 or 11 and 12 is higher. As shown in FIG. 4, an immovable fixed auxiliary arm 20 is provided at a position in the vicinity of each of the second robot arms 10, 11, and 12 and below each of the second robot arms 10, 11, and 12. The auxiliary arm 20 includes a fixed part 20A fixed to a fixing member 21, and a pair of grips 20B (in FIG. 4, only the grip 20B on the front side is shown) attached so as to be capable of moving close to and away from the fixed part 20A. FIG. 4 shows the state where, for example, after the upper end part of the preparation tank 18 is held by the second robot arm 10, 11, or 12, so as to be moved to a position where it can be gripped by the pair of grips 20B of the auxiliary arm 20, the lower end part of the preparation tank 18 is gripped by the pair of grips 20B of the auxiliary arm 20. In this way, a cap 18A of the preparation tank 18 can be opened or closed by the single second robot arm 10, 11, or 12. Further, a program to open and close screw caps that are provided on a plurality of types of containers is stored in the second robot arms 10, 11, and 12, so that the second robot arms 10, 11, and 12 can open and close the screw caps provided on the plurality of types of containers. Therefore, it is not necessary to unify the types of containers to be used in the production apparatus into the same type, and thus the production apparatus of cultured cell products can be easily achieved. Also in the first robot arms 6 and 7, such a program may be stored.

The two pass boxes 4, 4 are provided to be continuous with the rear wall of the processing section 13. One (on the left side) of the pass boxes 4 is arranged so that the articles can be carried therein passing through between the second robot arm 10 located at the left end and the second robot arm 11 located at the center. Examples of the articles include a plurality of types of containers including the product containers 9, the culture vessels 1, and the centrifuge tube 17, the preparation tank 18 that is a container in which drugs are put, and the like. The other (on the right side) of the pass boxes 4 is arranged so that the articles are carried to the second robot arm 12 located at the right end.

As described above, the isolator 3 is horizontally elongated, in which the plurality (in this embodiment, two) of pass boxes 4 are located on the longitudinal side of the isolator 3 (in this embodiment, on the rear side). This configuration can reduce the size of the production apparatus without limiting the amount of articles to be carried into the isolator 3.

The opening of the outlet 14 is configured to have a size such that the second robot arm 12 located at the right end can easily enter therethrough. The outlet 14 is provided with a freely openable electric shutter (not shown) and is provided continuously with the box 22 that forms a space in which the product containers 9 moved through the outlet 14 to the outside of the isolator 3 are kept for a while.

The processing section 13 includes a first transfer processing unit, a separation processing unit, and a second transfer unit. The first transfer processing unit is configured to transfer a cell-containing liquid housed in the culture vessels 1 received from the first robot arm 7 into the centrifuge tube 17 using the second robot arm 10. The separation processing unit is configured to separate the cells and a liquid portion by subjecting the centrifuge tube 17 to a centrifuge 26 using the second robot arm 10. The second transfer unit is configured to transfer a specified number of cells within the centrifuge tube 17 into a large number of the product containers 9 while a preservative solution (cryopreservation solution) is put into the centrifuge tube 17 after removing at least part of the liquid portion separated in the separation processing unit from the centrifuge tube 17, using the second robot arm 10. In the description of this embodiment, the term "cell-containing liquid" simply means a "liquid containing cells" and is not limited to a liquid in a specific state.

The processing section 13 includes a medium-replacing unit configured to replace the culture medium within the culture vessels 1 taken out of the incubators 2 using the first robot arm 7. The medium-replacing unit is configured to open the caps of the culture vessels 1 received by the second robot arm 10 from the first robot arm 7, to dispose of the culture medium within the culture vessels 1, to supply another culture medium into the culture vessels 1, to put the caps thereon, and to return them to the first robot arm 7.

The processing section 13 configured as above is capable of performing a first process of thawing frozen cells and seeding them, a second process (passage process) of collecting the cells and seeding them on a large number of culture vessels, and a third process of collecting the cultured cells in the culture vessels after the passage process, subdividing the collected cells, transferring them into the product containers 9, and carrying them out through the outlet 14.

Provided at a position close to the processing section 13 within the observation section 8 is a first disposal part 23 for disposal of waste products, which can be lid-closed, such as the centrifuge tube 17 and the preparation tank 18 (mainly those having a large size), in addition to the culture vessels 1, which have become unnecessary during the aforementioned various processes. Provided at a position close to the box 22 within the processing section 13 is a second disposal part 24 for disposal of, as waste products, articles (mainly those having a small size, but even for tips, there are large tips such as disposable tips), which cannot be lid-closed and therefore may cause dripping, such as pipette tips (suction openings mounted to pipettes, not shown), which have become unnecessary. Thus, the used centrifuge tube 17 or preparation tank 18 is carried from the pass box 4 on the left side into the isolator 3, as shown in, for example, FIG. 2. Then, the carried-in centrifuge tube 17 or preparation tank 18 is handled by the second robot arm 10 on the left side or the second robot arm 11 at the horizontal center, and is disposed of directly into the first disposal part 23 by the second robot arm 10 on the left side, or transferred from the second robot arm 10 on the left side to the first robot arm 7 on the right side and disposed of into the first disposal part 23 by the first robot arm 7. That is, the waste product, which is carried from the pass box 4 on the left side into the isolator 3 and used therein, is not returned from the isolator 3 toward the pass box 4 side, but is disposed of outside the isolator 3 through the first disposal part 23. Pipette tips after being used are carried from the pass box 4 on the right side into the isolator 3, as shown in, for example, FIG. 2, and handled by the second robot arm 12 on the right side and disposed of into the second disposal part 24. That is, the waste product after being used, which has been carried from the pass box 4 on the right side into the isolator 3, is not returned from the isolator 3 toward the pass box 4 side, but is disposed of outside the isolator 3 through the second disposal part 24.

Figure 5:
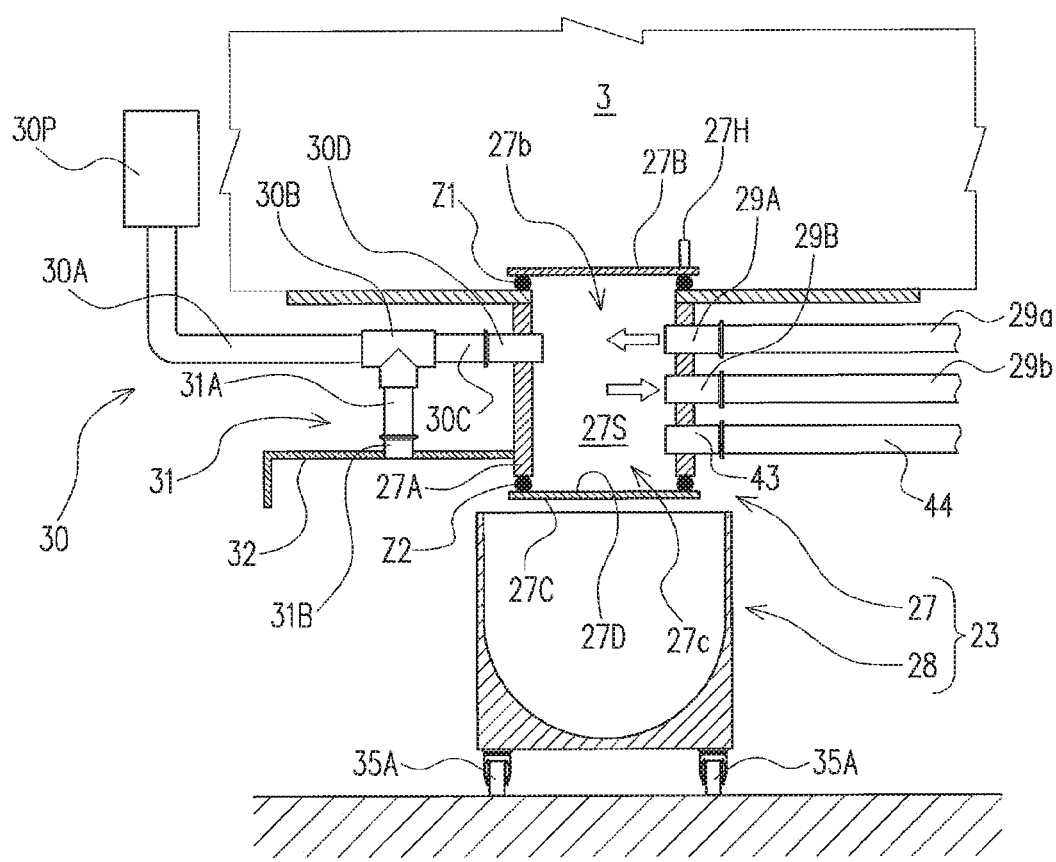
FIG. 5 is a vertical cross sectional front view of a disposal box, showing the state where the inside of the disposal box is being decontaminated.

As shown in FIG. 5, the first disposal part 23 includes a disposal box 27 having the storage part 27S that is sealable and configured to allow a waste product (description will be made herein by taking the culture vessel 1) to be once put thereinto and disposed of outside the isolator 3, and a waste product collecting container 28 of an upwardly open type arranged below the disposal box 27. In FIG. 5, the waste product collecting container 28 has a bottom plate part to which rollers 35A are attached so that the waste product collecting container 28 can be directly moved. However, the configuration may be such that the waste product collecting container 28 is placed on a carriage (not shown) provided with rollers so as to be movable. In FIG. 5, only two rollers 35A are shown, but the rollers 35A are provided at four corners (four places) of the waste product collecting container 28 in the actual configuration.

The disposal box 27 includes a vertically elongated tubular body 27A for forming the storage part 27S, a first lid 27B as a first opening and closing device for opening and closing an opening 27b at an upper end of the tubular body 27A, and a plate-shaped second lid 27C as a second opening and closing device for opening and closing an opening 27c at a lower end of the tubular body 27A. The upper end and the lower end of the tubular body 27A are respectively provided with seal members Z1 and Z2 for providing hermetical sealing between a lower end of the first lid 27B and an upper end of the second lid 27C.

The tubular body 27A has a supply port for decontamination 29A that supplies hydrogen peroxide gas ($H_2O_2$) to decontaminate the storage part 27S before a waste product is put from the isolator 3 thereinto, and a collection port for decontamination 29B that collects hydrogen peroxide gas ($H_2O_2$) supplied into the storage part 27S. As shown in FIG. 5 to FIG. 9, one ends of pipes 29a and 29b are respectively connected to the supply port for decontamination 29A and the collection port for decontamination 29B, and the second ends of the pipes 29a and 29b are connected to a hydrogen peroxide generator (not shown). The decontamination unit is constituted by the supply port for decontamination 29A, the collection port for decontamination 29B, the pipes 29a and 29b, and the hydrogen peroxide generator (not shown). Here, the storage part 27S is decontaminated using hydrogen peroxide gas, but decontamination can be made using ozone, chlorine dioxide gas, ethylene oxide gas, or the like. Another decontamination unit is provided separately from the decontamination unit for supplying a decontamination fluid (herein, hydrogen peroxide gas) into the storage part 27S to be arranged in or connected to the isolator 3 to allow the inside of the isolator 3 to be maintained in aseptic conditions by the other decontamination unit. The tubular body 27A has an exhaust port 43 that is configured to draw the gas supplied into the isolator 3 into the storage part 27S side by opening the first lid 27B and discharge the drawn gas to the outside. One end of a pipe 44 is connected to this exhaust port 43, and the other end of the pipe 44 is connected to an exhaust valve (not shown) communicating with an exhaust fan (not shown).

Connected to the disposal box 27 is an air supply unit for storage part 30 that supplies air into the storage part 27S of the disposal box 27 when the second lid 27C is opened to dispose of a waste product. This air supply unit for storage part 30 includes an air supply pump 30P, and a port for storage part 30D connected to the air supply pump 30P through a first pipe 30A, a T-shaped coupling 30B and a second pipe 30C. The port for storage part 30D is connected to the tubular body 27A to be communicated with each other.

An air supply unit for lid 31 is connected to the disposal box 27 to supply air onto a surface 27D located on the storage part 27S side of the second lid 27C at the time of disposal of a waste product by opening the second lid 27C. The air supply unit for lid 31 includes the aforementioned air supply pump 30P, and a port for second lid 31B that is connected to the air supply pump 30P through a pipe 31A branched from the aforementioned T-shaped coupling 30B. The port for second lid 31B is communicatively connected from above to an overhang 32, the overhang 32 being provided to cover above the second lid 27C that horizontally extends from a lower part of an outer lateral surface of the tubular body 27A and is held in the opened state.

The first lid 27B is configured to be horizontally slidable, and, at the time when a waste product is to be received into the storage part 27S from the isolator 3, the control unit X outputs a command signal so that the second robot arm 10 holds a handle 27H and slide the first lid 27B to perform the opening operation (see FIG. 6), so that the isolator 3 and the storage part 27S can be communicated with each other. After the receiving of the waste product 1 but before the disposal, the robot arm 10 holds the handle 27H and slides the first lid 27B to perform the closing operation (see FIG. 7), so that the isolator 3 and the storage part 27S can be shut off from each other. The second lid 27C is configured to be horizontally slidable by the extension and retraction of an air cylinder (not shown), and at the time when the waste product 1 put into the storage part 27S is to be disposed of outside, the control unit X outputs a command signal so that the air cylinder is retracted to slide the second lid 27C to perform the opening operation (see FIG. 8), so that the storage part 27S and the outside can be communicated with each other. After the disposal of the waste product 1, the air cylinder is extended to slide the second lid 27C to perform the closing operation (see FIG. 9), so that the storage part 27S and the outside can be shut off from each other. Here, the second lid 27C is opened and closed using the air cylinder, but such opening and closing may be made using a different actuator such as a hydraulic cylinder and an electric motor.

Figure 6:
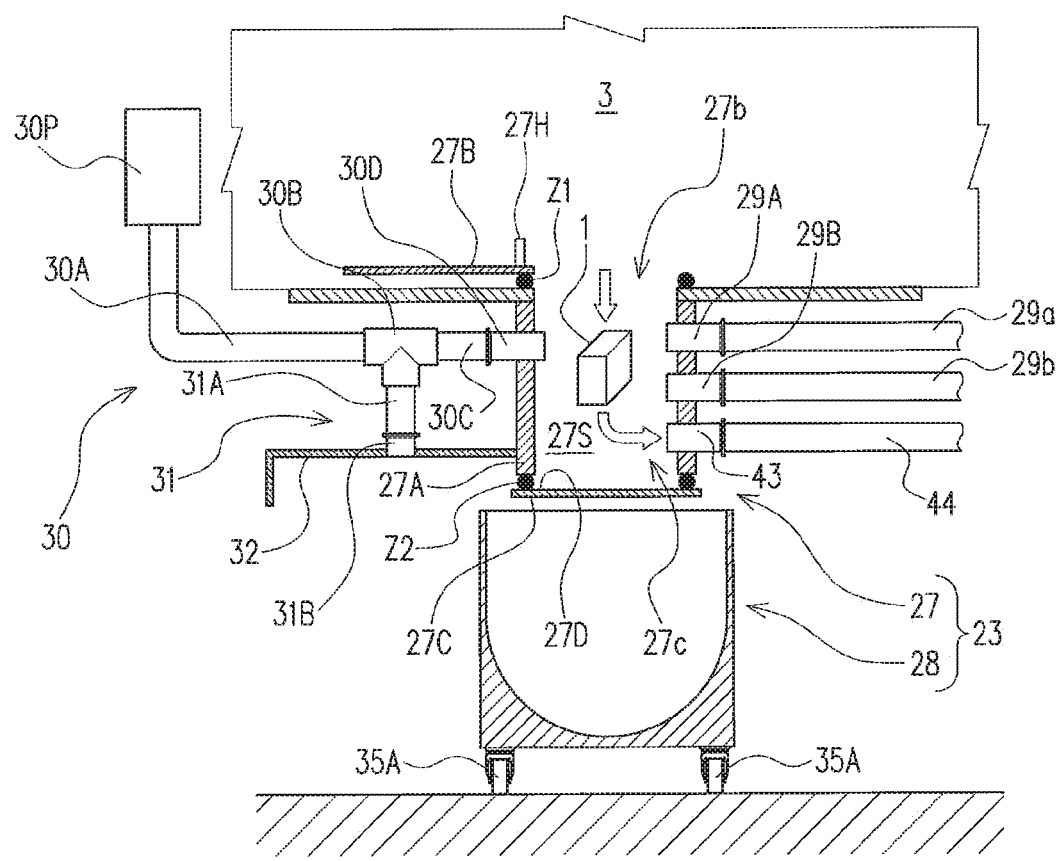
FIG. 6 is a vertical cross sectional front view of the disposal box, showing the state where a waste product has been stored in the disposal box.
Figure 7:
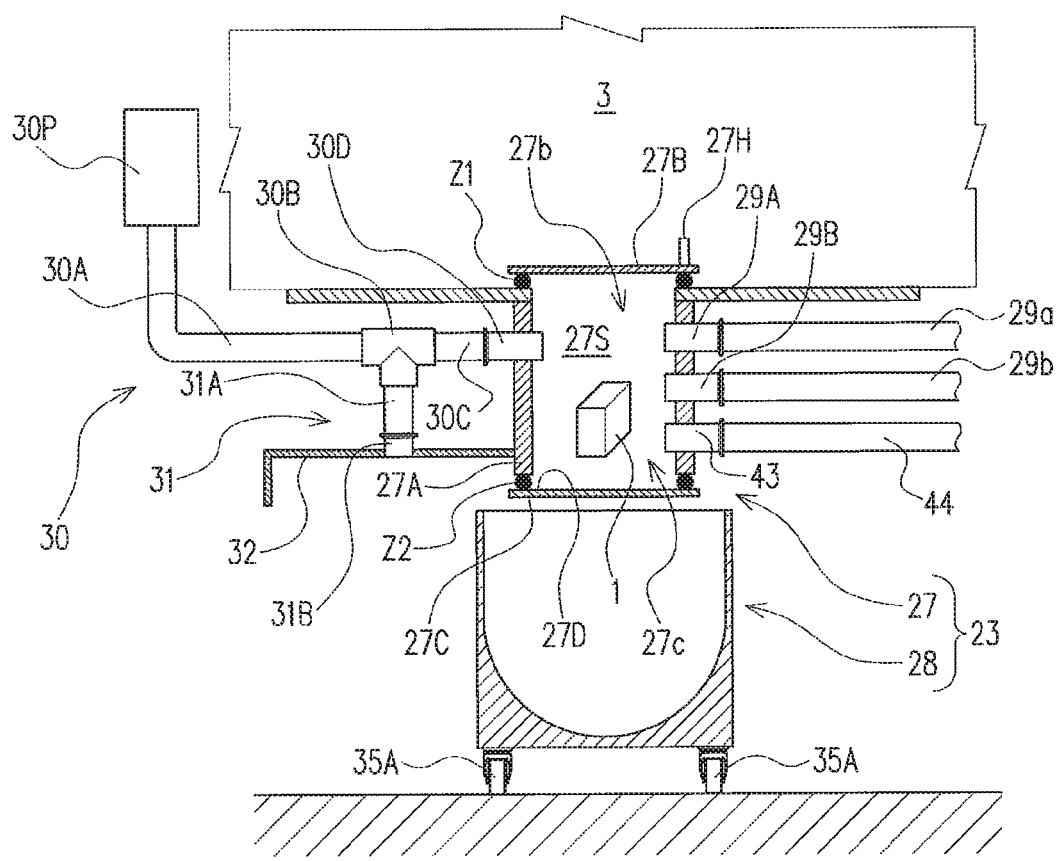
FIG. 7 is a vertical cross sectional front view of the disposal box, showing the state where a waste product is stored under sealed conditions in the disposal box.
Figure 8:
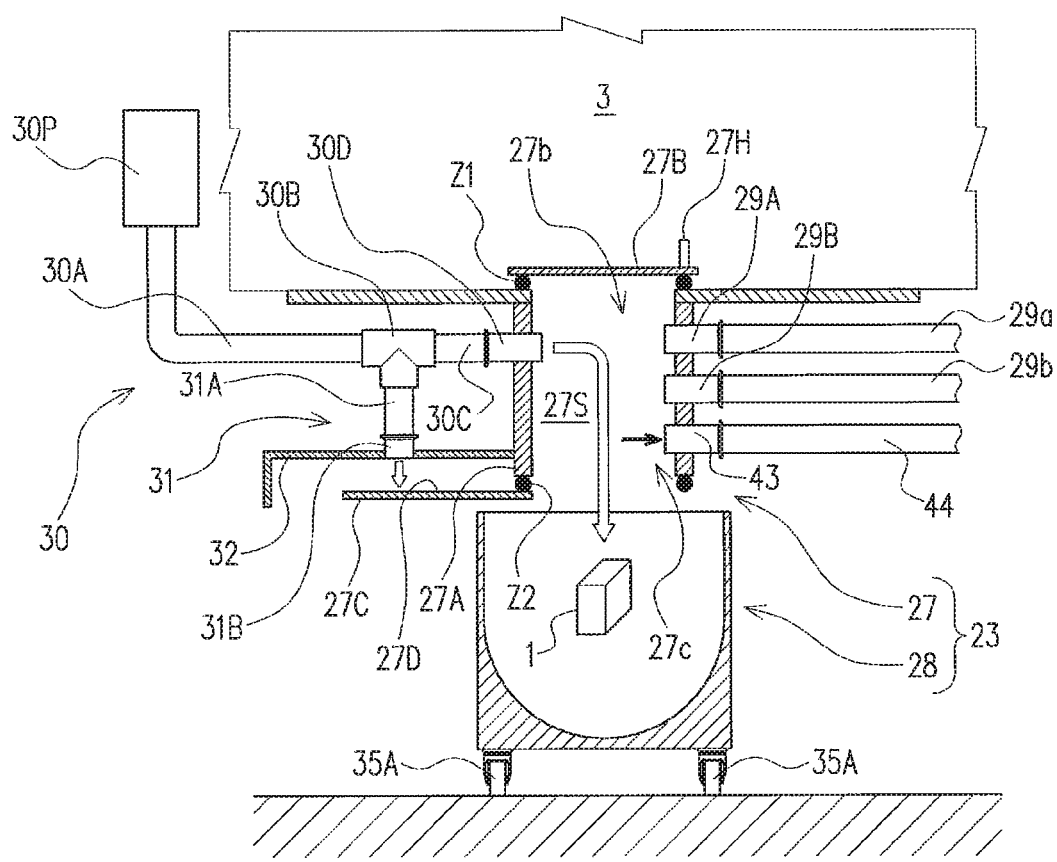
FIG. 8 is a vertical cross sectional front view of the disposal box, showing the state where a waste product stored in the disposal box is being disposed of outside.
Figure 9:
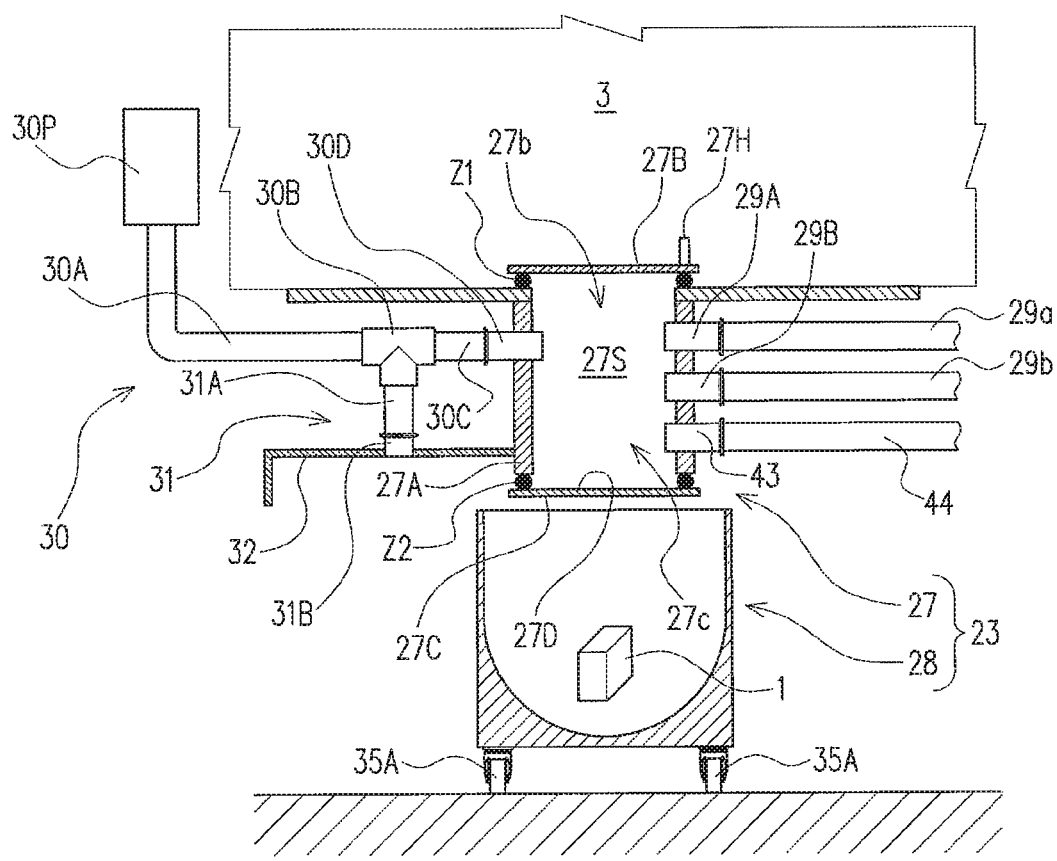
FIG. 9 is a vertical cross sectional front view of the disposal box, showing the state where a waste product has been stored in a disposal container arranged outside.

The procedures for disposing of a waste product, which can be lid-closed (has a configuration capable of preventing dripping), will be explained with reference to FIG. 5 to FIG. 9. FIG. 5 shows the state before a waste product is disposed of. When the first lid 27B and the second lid 27C are held in closed state, hydrogen peroxide is supplied from the supply port for decontamination 29A to the storage part 27S, and collected through the collection port for decontamination 29B so that the inside of the storage part 27S is decontaminated. After the completion of decontamination, the control unit X outputs a command signal to command the second robot arm 10 on the left side or the first robot arm 7 on the right side to dispose of the waste product, so that, as shown in FIG. 6, the second robot arm 10 or the first robot arm 7 holds the handle 27H to open the first lid 27B and puts the waste product 1 into the opening 27*b*. At this time, the gas supplied into the isolator 3 is drawn into the storage part 27S through the exhaust port 43 and is exhausted to the outside through the exhaust port 43, so that gas flows flowing from the isolator 3 toward the storage part 27S side are generated. Whereby it is possible to maintain the inside of the isolator 3 in aseptic conditions, while preventing generation of gas flows from the storage part 27S toward the inside of the isolator 3. It may be configured to supply a small amount of clean air from the port for storage part 30D into the storage part 27S so as to make it easy for air to flow from the isolator 3 toward the storage part 27S side. As shown in FIG. 7, after the waste product 1 has been put in, the second robot arm 10 or the first robot arm 7 again holds the handle 27H to close the first lid 27B. Subsequently, as shown in FIG. 8, the second lid 27C is opened by the air cylinder to dispose of the waste product 1 into the downward waste product collecting container 28 by falling, and clean air from the port for storage part 30D and the port for second lid 31B is supplied into the storage part 27S and onto the surface 27D (the upper surface in Figure) on the storage part 27S side of the second lid 27C in the opened state. The amount of gas exhausted from the exhaust port 43 at this time is set to be smaller than the amount of gas exhausted therefrom at the time when the gas supplied into the isolator 3 is drawn into the storage part 27S as mentioned above, so that gas flows from the port for storage part 30D to the outside (lower side) of the storage part 27S are not hindered. Also, supplying of clean air mentioned above can suppress contaminated air from entering the storage part 27S from the outside and outside contaminated air from contacting the surface 27D on the storage part 27S side of the second lid 27C. After the disposal of the waste product 1, the second lid 27C is closed by the air cylinder and then supplying of clean air is stopped (see FIG. 9).

Figure 10:
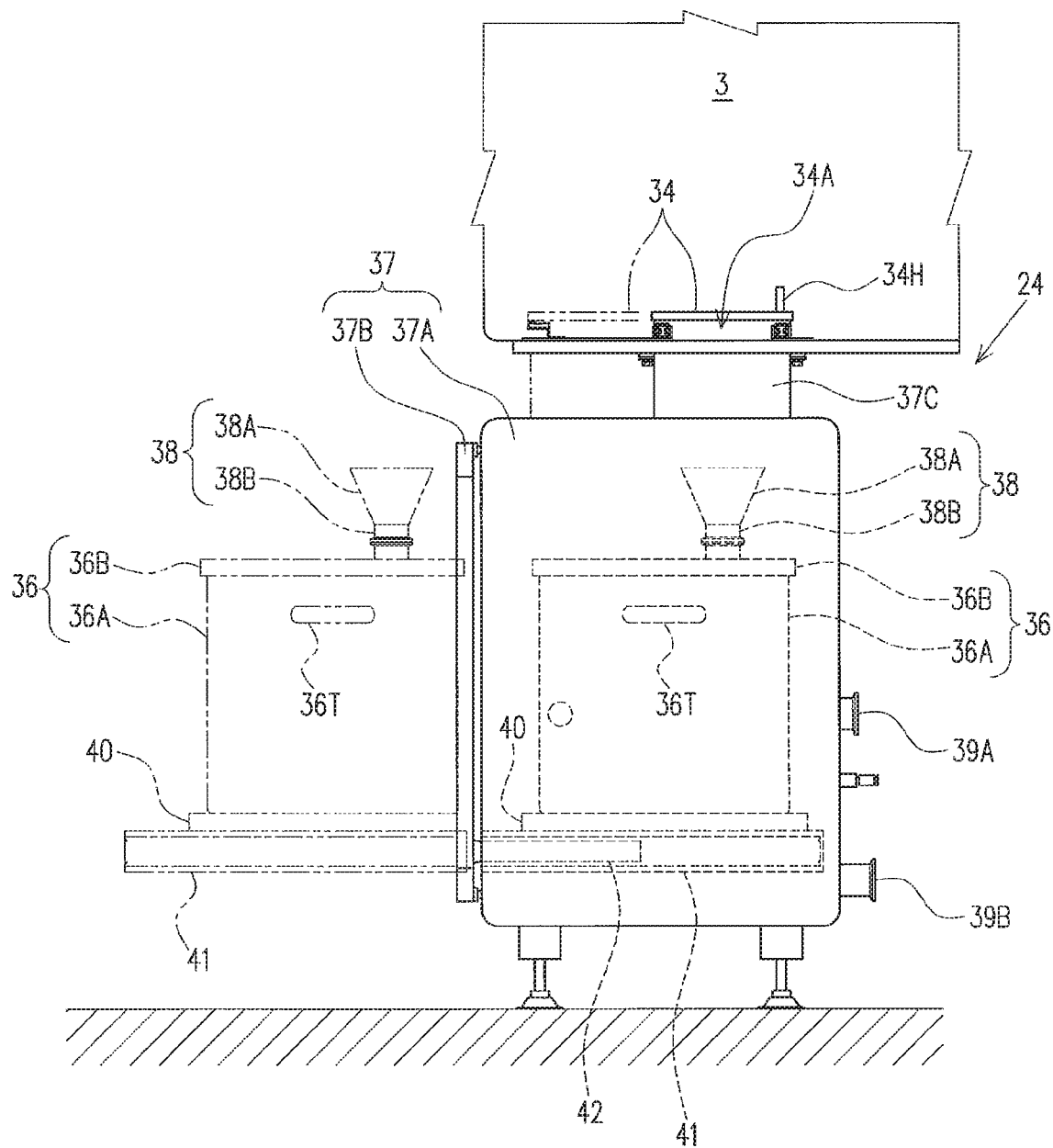
FIG. 10 is a vertical cross sectional side view of a second disposal part.

As shown in FIG. 10, the second disposal part 24 includes an opening and closing lid 34 that opens and closes an opening 34A, through which a waste product (herein, not shown pipette tips) is put into the second disposal part 24, a collection box 36 that is arranged below the opening 34A to receive and collect the put-in waste product, and a decontamination box 37 that brings the collection box 36 into sealed conditions to decontaminate the same.

The opening and closing lid 34 is configured to be horizontally slidable and includes a handle 34H projecting from an upper surface. The second robot arm 12 on the right side (or the second robot arm 11 in the middle) holds this handle 34H and moves the opening and closing lid 34 to an opening position shown in two-dot chain line and a closing position shown in solid line.

The collection box 36 includes a box body 36A having an upwardly-opening bottomed cylindrical shape, and a lid 36B that closes an upper end opening of the box body 36A, and a guide 38 that is arranged at an upper end of the lid 36B to guide a waste product which has been put and dropped from the opening 34A, to the box body 36A. The guide 38 includes a receiving part 38A having such a shape as to be radially increased as it advances upward, and a cylindrical part 38B that extends downward from a lower end of the receiving part 38A and is communicatively connected to the lid 36B. A pair of handles 36T. 36T (only one of them is shown in Figures) are attached to lateral sides of the box body 36A.

The decontamination box 37 includes a box part 37A that has an opening for inputting and outputting the collection box 36 and has a rectangular shape in planer view, and a door 37B that is attached to the box part 37A to be openable and closable around a vertical axis to close the opening of the box part 37A.

A tubular part 37C having an angular shape for guiding a waste product to be put from the opening 34A into the box part 37A is provided at an upper end of the box part 37A. Provided on a side opposite to the door 37B of the box part 37A are a supply port for decontamination 39A for supplying hydrogen peroxide gas ($H_2O_2$) for decontaminating the inside of the box part 37A, and a collection port for decontamination 39B for collecting the supplied hydrogen peroxide gas ($H_2O_2$). A mounting table 40 on which the collection box 36 is mounted is provided in the box part 37A, and slide rails 42, 42 (only one is shown in FIG. 10) are attached to the opposite side portions of the mounting table so as to be slidably engaged with a pair of guide rails 41, 41 (only one is shown in FIG. 10) attached to a lower portion of opposite inner surfaces of the box part 37A. Accordingly, it is possible to easily take out the collection box 36 by opening the door 37B and slidingly moving the mounting table 40 to the outside the box part 37A. Here, the inside of the box part 37A is decontaminated using hydrogen peroxide gas, but decontamination may be made using ozone, chlorine dioxide gas, ethylene oxide gas, or the like.

The description will be made for the procedures for disposing of a waste product which cannot be cap-covered and therefore may cause dripping. The control unit X outputs a command signal to dispose of a waste product which cannot be cap-covered and therefore may cause dripping, and then determines whether the inside of the decontamination box 37 has been decontaminated, and when it determines that the decontamination has been made, the control unit X outputs a command signal to the second robot arm 11 or 12 to dispose of the waste product. The second robot arm 11 or 12, upon receiving the command signal, holds the handle 34H to open the opening and closing lid 34 and puts in the waste product through the opening 34A. The put-in waste product passes through the tubular part 37C, and is guided into the collection box 36 by the guide 38 so as to be stored therein. Subsequent to the storage of the waste product, the second robot arm 11 or 12 holds the handle 34H to close the opening and closing lid 34 held in the opened state. When a certain amount of waste products are stored in the collection box 36, the worker as the operator opens the door 37B, pulls out the mounting table 40 forward, takes out the collection box 36, and transfers it to another disposal box (not shown), or conveys the collection box 36 in sealed conditions to a certain position. A pipette tip has a solution remaining therein, and therefore the solution leaked from the pipette tip adheres to the inside of the collection box 36. Thus, in the case where the collection box 36 is again used, it is subjected to sterilization or decontamination treatment.

The apparatus for producing cultured cell products according to the present invention is not limited to the aforementioned embodiment, and various modifications can be made without departing from the gist of the present invention.

The aforementioned embodiment was described by taking, for example, the case where the two robot arms 6 and 7 are provided in the observation section 8, and the three robot arms 10, 11, and 12 are provided in the processing section 13. However, it is also possible to apply, to the present invention, the configuration of providing at least one robot arm in the observation section 8 and providing at least one robot arm in the processing section 13.

In the aforementioned embodiment, the isolator 3 is configured to have a horizontally elongated shape as an example, but may be configured to have a square shape or a circular shape. Further, it may be configured to have a bent shape.

In the aforementioned embodiment, the microscopes 16 and 25 are used for observing cells, but it is not necessary to limit to the microscope, and various image magnification devices that can magnify an image capturing cells as observation targets can be used. It is possible to accurately count the number of living cells by using the image magnification device.

The aforementioned embodiment was described by taking, for example, the case where one first disposal part 23 is provided and one second disposal part 24 is provided. However, at least one of the first disposal part 23 and the second disposal part 24 may comprise plural disposal parts.

In the aforementioned embodiment, the second disposal part 24 is configured be able to be decontaminated, but may be configured to be disable to be decontaminated. In this case, the configuration is such that a container, which houses the second disposal part 24 having waste products accumulated therein cannot be taken out to the outside, and, when prefixed treatments have been all finished, the second disposal part 24 is detached from the isolator 3 to allow the waste products to be disposed of. Therefore, it is necessary to take a measure, namely by providing plural second disposal parts 24 or increasing the capacity of the second disposal part 24.

The aforementioned embodiment was described by taking, for example, the case where the air supply unit for storage part 30 and the air supply unit for lid 31 are provided. However, the present invention can be carried out by eliminating one or both units.

In the aforementioned embodiment, the first opening and closing device 27B and the second opening and closing device 27C, and the opening and closing lid 34 of the second disposal part 24 are configured to be of a sliding type that move in the horizontal direction. However, they may be configured to be of a pivotal type that opens and closes around a vertical axis or a horizontal axis. In addition to the configuration that the first opening and closing device 27B and the opening and closing lid 34 are opened and closed by the robot arms, the opening and closing of the first opening and closing device 27B and the opening and closing lid 34 may be made using a power exerted by an actuator.

In the aforementioned embodiment, two systems of the decontamination units are respectively provided in the isolator 3 and the storage part 27S so that the timing of decontamination in the storage part 27S can be freely adjusted. However, it may be configured so that the decontamination unit is arranged in or connected to the isolator 3 to allow part of a decontamination fluid supplied to the isolator 3 to be branched to be supplied into the storage part 27S. In this case, it is possible to more easily simplify the configuration than the configuration that the decontamination units are separately provided in the isolator 3 and the storage part 27S.

The description of the aforementioned embodiment was made for the apparatus to produce cultured cell products, which is configured to culture cells and subdivide cultured cells into products. However, the present invention is also applicable to an apparatus to culture cells, which is configured to perform only cell culturing, or applicable to a product manufacturing apparatus, which is configured to subdivide cultured cells into products.

The configuration and action of the aforementioned embodiment will be summarized below. The cell treatment apparatus according to the present embodiment includes: an isolator 3 that has an inner space maintained in aseptic conditions and is configured to treat cells in the inner space; a disposal box 27 that includes a storage part 27S that can be sealed and is configured to allow a container, which contains a reagent for use in treatment of cells in the inner space of the isolator 3 and has become no longer needed as a result of use of the reagent, to be once put thereinto as a waste product 1 and then be disposed of outside the isolator; and a decontamination unit for decontaminating the storage part 27S, wherein the disposal box 27 includes: a first opening and closing device 27B that is openable and closable, and is configured to allow the isolator 3 and the storage part 27S to be communicated with each other at the time of disposal of the waste product 1 and allow them to be shut off from each other after the putting-in of the waste product 1 and before the disposal of the same; and a second opening and closing device 27C that is openable and closable, and is configured to allow the storage part 27S and the outside to be communicated with each other at the time of disposal of the waste product 1, which has been put into the storage part 27S, and allow them to be shut off from each other after the disposal of the waste product 1.

According to the above configuration, the container, which has become no longer needed as a result of use of the reagent, can be disposed of outside through the disposal box 27 as a waste product, while having the inner space of the isolator (treatment apparatus) 3 maintained in aseptic conditions, during treatment of cells. That is, the container, which has become no longer needed as a result of the use of the reagent, is put into the disposal box 27. This disposal box 27 is held in decontaminated conditions by the decontamination unit. In the decontaminated conditions, the first opening and closing device 27B is opened to put the waste product 1 into the storage part 27S within the disposal box 27 so that the inner space of the isolator 3 can be maintained in aseptic conditions. When the waste product 1 is stored in the storage part 27S within the disposal box 27, the waste product 1 can be stored in the storage part 27S of the disposal box 27 in sealed conditions until the disposal of the waste product 1 by closing the first opening and closing device 27B. Next, the waste product 1 stored in the storage part 27S can be disposed of outside the disposal box 27 by opening the second opening and closing device 27C. After the disposal of the waste product 1, the second opening and closing device 27C is held at the closing position so as to be in a standby state until the next disposal of a waste product.

The cell treatment apparatus according to the aforementioned embodiment may be configured to include an air supply unit for storage part 30 that supplies air into the storage part 27S when the second opening and closing device 27C is opened and the waste product 1 is disposed of.

According to the aforementioned configuration, when the second opening and closing device 27C is opened and the waste product 1 is disposed of, that is, when the inner space of the disposal box 27 and the outside of the disposal box 27 are brought into communication with each other, it is possible to suppress intrusion of contaminated air from the outside into the storage part 27S by supplying air into the storage part 27S by the air supply unit for storage part 30.

In the cell treatment apparatus according to the aforementioned embodiment, it may be configured so that the second opening and closing device 27C is formed by a plate-shaped lid that can open and close an opening 27c formed at a lower end of the storage part 27S, and an air supply unit for lid 31 is further included, which supplies air onto a surface 27D which is located on the storage part side of the lid when the lid is opened and the waste product is disposed of.

According to the aforementioned configuration, when the lid of the second opening and closing device 27C is opened and the waste product 1 is disposed of, the air supply unit for lid 31 supplies air onto the surface 27D which is located on the storage part side of the lid so that outside contaminated air can be suppressed from contacting the surface 27D which is positioned on the storage part side of the lid.

It is preferable that the cell treatment apparatus according to the aforementioned embodiment is configured so that the waste product 1 includes a container body 1A, and a cap 1B for covering an opening of the container body 1A and thereby sealing the inside thereof, and the waste product 1 is disposed of with the inside of the container body 1A being sealed by the cap 1B.

According to the aforementioned configuration, when the waste product 1 is disposed of, it is held in sealed conditions by sealing with the cap 1B, and therefore it is possible to prevent occurrence of leakage of a liquid remaining within the waste product 1 to the outside and hence adhering to the inside of the storage part 27S. Thus, it is possible to suppress contamination of the inside of the storage part 27S due to a liquid leaked from the waste product 1 to the outside.

In the cell treatment apparatus according to the aforementioned embodiment, the decontamination unit may be connected to the storage part 27S.

According to the aforementioned configuration with the decontamination unit being connected to the storage part 27S, it is possible to freely adjust the timing of decontamination by the decontamination unit, and hence increase the treatment efficiency.

The cell treatment apparatus according to the aforementioned embodiment may be configured so that the decontamination unit is arranged in or connected to the isolator 3 so that part of a decontamination fluid supplied from the decontamination unit to the isolator 3 is supplied into the storage part 27S.

According to the aforementioned embodiment, it is possible to more easily simplify the configuration by supplying part of a decontamination fluid, which is supplied from the decontamination unit into the isolator 3, into the storage part 27S than the configuration that the decontamination units are separately provided in the isolator 3 and the storage part 27S.

It is preferable that the cell treatment apparatus according to the aforementioned embodiment includes a pass box 4 for carrying the container into the isolator 3, and the container, which has been carried into the pass box 4 and used, is put into the disposal box 27.

According to the aforementioned configuration, the container which has been carried in from the pass box 4 and used, is put into the disposal box 27 and disposed of outside the isolator 3, so that the container as the waste product is not returned to the pass box 4 side.

As described above, in the aforementioned embodiment, it is possible to dispose of the waste product outside the apparatus through the disposal box 27, while having the inside of the treatment apparatus maintained in aseptic conditions so that there is no need to suspend the treatment. Thus, it is possible to provide the cell treatment apparatus that can perform treatments in an efficient manner.

REFERENCE SIGNS LIST

1: Cell culture vessel (Waste product)
1A: Container body
1B: Cap
2: Incubator
2A: Casing
2B, 2C: Door
3: Isolator
4: Pass box
5: Mounting table
6, 7: First robot arm
6A: Fixed part
6B: Base part
6C: First arm
6D: Second arm
6E: Third arm
6F: Grip
8: Observation section
9: Product container
10, 11, 12: Second robot arm
13: Processing section
14: Outlet
15: Base member
16: Microscope
17: Centrifuge tube
18: Preparation tank
18A: Cap
19: Conveying apparatus
20: Auxiliary arm
20A: Fixed part
20B: Grip
21: Fixing member
22: Box
23: First disposal part
24: Second disposal part
25: Microscope
26: Centrifuge
27: Disposal box
27A: Tubular body
27B: First opening and closing device (First lid)
27C: Second opening and closing device (Second lid)
27D: Surface
27H: Handle
27S: Storage part
27b: Opening
27c: Opening
28: Waste product collecting container
29A: Supply port for decontamination
29a, 29b: Pipe
29B: Collection port for decontamination
30: Air supply unit for storage part
30A: Pipe
30B: T-shaped coupling
30C: Pipe
30D: Port for storage part
30P: Air supply pump
31: Air supply unit for lid
31A: Pipe
31B: Port for second lid
32: Overhang
34: Opening and closing lid
34A: Opening
34H: Handle
35: Carriage
35A: Roller
36: Collection box
36A: Box body
36B: Lid
36T: Handle
37: Decontamination box 37A: Box part
37B: Door
37C: Tubular part
38: Guide
38A: Box part
38B: Cylindrical part
39A: Supply port for decontamination
39B: Collection port for decontamination
40: Mounting table
41: Guide rail
42: Slide rail
X: Control unit
Z1, Z2: Seal material

The invention claimed is:

1. A cell treatment apparatus comprising:
an isolator that has an inner space maintained in aseptic conditions and is configured to treat cells in the inner space;
a disposal box that includes a storage part that can be sealed and is configured to allow a container, which contained a reagent for use in treatment of cells in the inner space of the isolator and has become no longer needed as a result of use of the reagent, to be once put thereinto as a waste product and then be disposed of outside the isolator; and
a decontamination unit for decontaminating the storage part, wherein
the disposal box comprises: a first opening and closing device that is openable and closable, and is configured to allow the isolator and the storage part to be communicated with each other at the time of disposal of the waste product and allow them to be shut off from each other after the putting-in of the waste product and before the disposal of the same; and a second opening and closing device that is openable and closable, and is configured to allow the storage part and the outside to be communicated with each other at the time of disposal of the waste product, which has been put into the storage part, and allow them to be shut off from each other after the disposal of the waste product, wherein
the cell treatment apparatus further comprises an air supply unit for the storage part wherein
the air supply unit is directly connected to the disposal box, wherein
the air supply unit is configured to allow ventilation by suppling air into the storage part when the first opening and closing device is closed and the second opening and closing device is opened and the waste product is disposed of, wherein
the air supply unit comprises a port for the storage part, and the port for the storage part is connected to a tubular body of the disposal box to be communicated with each other.

2. The cell treatment apparatus according to claim 1, wherein the second opening and closing device is formed by a plate-shaped lid that can open and close an opening formed at a lower end of the storage part, and the apparatus further comprises an air supply unit for the lid that supplies air onto a surface which is located on the storage part side of the lid when the lid is opened and the waste product is disposed of.

3. The cell treatment apparatus according to claim 2, wherein the air supply unit for the storage part further comprises an air supply pump, a first pipe, a coupling and a second pipe, wherein
the port for storage part is connected to the air supply pump through the first pipe, the coupling and the second pipe, wherein
the air supply unit for lid comprises a pipe branched from the coupling, and a port for second lid, wherein
the port for second lid is connected to the air supply pump through the coupling and the pipe.

4. The cell treatment apparatus according to claim 1, wherein the waste product comprises a container body, and a cap for closing an opening of the container body and thereby sealing the inside thereof, and the waste product is disposed of with the inside of the container body being sealed by the cap.

5. The cell treatment apparatus according to claim 1, wherein the decontamination unit is connected to the storage part.

6. The cell treatment apparatus according to claim 1, wherein the decontamination unit is arranged in or connected to the isolator so that part of a decontamination fluid supplied from the decontamination unit to the isolator is supplied into the storage part.

* * * * *